US006638892B1

(12) United States Patent
Wu et al.

(10) Patent No.: US 6,638,892 B1
(45) Date of Patent: Oct. 28, 2003

(54) SYNGAS CONVERSION AND CATALYST SYSTEM EMPLOYED THEREFOR

(75) Inventors: An-hsiang Wu, Kingwood, TX (US); Jianhua Yao, Bartlesville, OK (US); Charles A. Drake, Nowata, OK (US)

(73) Assignee: ConocoPhillips Company, Houston, TX (US)

( * ) Notice: Subject to any disclaimer, the term of this patent is extended or adjusted under 35 U.S.C. 154(b) by 0 days.

(21) Appl. No.: 10/125,661

(22) Filed: Apr. 18, 2002

(51) Int. Cl.[7] .......................... B01J 23/00; B01J 29/08; B01J 21/16; B01J 27/14; B01J 27/182
(52) U.S. Cl. .................. 502/307; 502/306; 502/314; 502/318; 502/79; 502/80; 502/208; 502/214
(58) Field of Search ................................ 502/306, 318, 502/314, 80, 79, 208, 214, 307

(56) References Cited

U.S. PATENT DOCUMENTS

| | | |
|---|---|---|
| 3,911,041 A | 10/1975 | Kaeding et al. |
| 4,375,424 A | 3/1983 | Slaugh |
| 4,423,155 A | 12/1983 | Bell et al. |
| 4,499,327 A | 2/1985 | Kaiser |
| 4,536,485 A | 8/1985 | Topp-Jorgensen |
| 4,590,176 A | 5/1986 | Hoek et al. |
| 4,613,720 A | 9/1986 | Bonifaz et al. |
| 4,849,575 A | 7/1989 | Lewis |
| 5,182,242 A | 1/1993 | Marler |
| 5,191,141 A | 3/1993 | Barger et al. |
| 5,218,003 A | 6/1993 | Lewnard et al. |
| 5,684,213 A | 11/1997 | Nemphos et al. |
| 5,714,662 A | 2/1998 | Vora et al. |
| 6,048,816 A | * 4/2000 | Brown et al. .................. 502/77 |
| 6,137,022 A | * 10/2000 | Kuechler et al. ............ 585/638 |
| 6,147,125 A | * 11/2000 | Shikada et al. ............. 518/713 |

OTHER PUBLICATIONS

Decanio et al, Acid Catalysis by Dealuminated Zeolite–Y, Journal of Catalysis 101, 132–141 (1986).*

* cited by examiner

Primary Examiner—J. Parsa
(74) Attorney, Agent, or Firm—Ryan N. Cross

(57) ABSTRACT

A process for the conversion of syngas by contact of syngas under conversion conditions with catalyst having as components zinc oxide, copper oxide, aluminum oxide, Y zeolite and clay in which (A) in a one step process for conversion of syngas to dimethyl ether, the catalyst has as components an extruded mixture of zinc oxide, copper oxide, gamma aluminum oxide, Y zeolite and clay; (B) in a two step process for conversion of syngas to light olefins, a catalyst system is employed that has in the first step a catalyst mixture of zinc oxide, copper oxide, aluminum oxide, Y zeolite and clay and the catalyst employed in the second step is SAPO-34; SAPO-34 modified with lanthanum(III) nitrate hexahydrate; SAPO-34 modified with magnesium nitrate hexahydrate; SAPO-34 modified with tributyl borate or SAPO-34 modified with triethyl phosphate or (C) in a two step process for conversion of syngas to light olefins, the pressure on the effluent from the contact of syngas with a mixture of zinc oxide, copper oxide, aluminum oxide, Y zeolite and clay is reduced before contact with a second catalyst of SAPO-34. The catalyst systems employed in the processes herein.

8 Claims, No Drawings

SYNGAS CONVERSION AND CATALYST SYSTEM EMPLOYED THEREFOR

FIELD OF THE INVENTION

This invention relates to a catalyst composition having as components zinc oxide, copper oxide and aluminum oxide in combination with Y zeolite and clay suitable for the conversion of syngas, a mixture of hydrogen and carbon monoxide, to dimethyl ether and to the process for converting synthesis gas (syngas) to dimethyl ether employing this catalyst. This invention also relates to two-step processes for converting syngas to light olefins by contacting the effluent from a conversion of syngas employing a catalyst composition having as components zinc oxide, copper oxide and aluminum oxide in combination with Y zeolite and clay with a second catalyst system having a SAPO component such as, in particular, SAPO-34 or modified SAPO-34. This invention is further related to catalyst systems useful in the conversion of syngas to light olefins in two step processes.

BACKGROUND OF THE INVENTION

Catalysts having zinc oxide, copper oxide and aluminum oxide as components are known to be effective as methanol synthesis catalysts. Catalysts having as components zinc oxide, copper oxide and aluminum oxide or chromium oxide in conjunction with a gamma aluminum oxide are known to effect the conversion of syngas to dimethyl ether. The present invention provides an improved conversion and selectivity to dimethyl ether by replacing gamma aluminum oxide with a combination of Y zeolite and clay in a catalyst system useful for the conversion of syngas.

Processes for converting methanol and its derivatives, including dimethyl ether, to light olefins employing a SAPO catalyst are also known. U.S. Pat. No. 4,499,327 discloses the preparation of light olefins from dimethyl ether or methanol employing a SAPO catalyst, but does not disclose the preparation of dimethyl ether using the process cited above.

There is a growing interest in alternative liquid fuels produced from natural gas. Dimethyl ether is a clean and efficient alternative diesel fuel which can be produced by the dehydration of methanol which can be synthesized from syngas. There is a significant economic advantage in integrating the process for producing dimethyl ether from syngas into a single process. There is also a continued expansion of the uses to which light olefins can be put and therefore a commercial reward for improving the methods by which light olefins can be produced. Syngas has proved to be an attractive source from which light olefins can be obtained. Accordingly, development of these improved processes for converting syngas to dimethyl ether or light olefins and development of the catalyst systems useful in these processes would be a significant contribution to the art.

SUMMARY OF THE INVENTION

It is an object of this invention to provide an improved method for converting syngas to dimethyl ether. It is another object of this invention to use this improved process in two step processes for the conversion of syngas to light olefins. Still another object of this invention is to employ SAPO in the second step of converting dimethyl ether to light olefins in these two step processes for converting syngas to light olefins. Another object of the invention is to provide methods for converting dimethyl ether to light olefins that show improved results employing modified SAPO-34 as compared to the use of SAPO-34 in a two step process. A yet further object of this invention is to provide the catalyst systems useful in the conversions set out above. Other objects and advantages will be apparent from the detailed description and the appended claims.

In accordance with an embodiment of this invention a method is provided for converting syngas by contacting syngas under conversion conditions with a catalyst comprising zinc oxide, copper oxide, aluminum oxide, Y zeolite and clay.

In accordance with another embodiment of this invention a method is provided for the conversion of syngas to dimethyl ether (DME) by contacting syngas under conversion conditions with a catalyst comprising zinc oxide, copper oxide, aluminum oxide, Y zeolite and clay.

In accordance with still another embodiment of this invention a method is provided for the conversion of syngas to light olefins by contacting syngas under conversion conditions with (A) a first catalyst comprising zinc oxide, copper oxide, aluminum oxide, Y zeolite and clay under conditions for the conversion of syngas to dimethyl ether and then contacting the effluent from contact with the first catalyst with (B) a second catalyst comprising SAPO under conditions for the conversion of dimethyl ether to light olefins.

In accordance with other embodiments of this invention methods are provided for the conversion of syngas to light olefins in which the second catalyst is SAPO-34 and (1) the temperature of the second step is increased as compared to the temperature of the first step or (2) the temperature of the second step is increased as compared to the temperature of the first step and the pressure of the effluent from the contact with the first catalyst is reduced before contact with the second catalyst.

In accordance with other embodiments of this invention methods are provided for the conversion of syngas to light olefins in which the second catalyst is a modified SAPO-34 such as SAPO-34 modified with lanthanum(III) nitrate hexahydrate; SAPO-34 modified with magnesium hydrate hexahydrate; SAPO-34 modified with tributyl borate or SAPO-34 modified with triethyl phosphate.

Other objects and advantages of the invention will become apparent from the detailed description and the appended claims.

DETAILED DESCRIPTION OF THE INVENTION

For the purposes of this disclosure the citing in the specification, claims or abstract of a component or components should be construed as including a restrictive phrase chosen from among the following: in the broadest sense as not excluding the presence of other components, i.e. "comprising"; in a more restricted sense as containing only the material cited as essential to the invention with no other material present in an amount to affect the invention, i.e. "consisting essentially of", and in the most restricted sense as the presence of only the material cited, i.e. "consisting of". The use of any of the quoted phrases limits the disclosed component or components in the sense defined above.

Synthesis gas (syngas) is a gaseous mixture of hydrogen and at least one carbon oxide, particularly carbon monoxide. Syngas is obtained using well known processes by the partial combustion or gasification of any organic material such as coal, other hydrocarbons, carbohydrates and the like. It is well known that Syngas can be subjected to a heterogeneous catalytic reaction using a copper-based catalyst such as copper oxide, zinc oxide and aluminum oxide to produce methanol. This is the same catalyst that is used in this invention along with Y zeolite and clay to produce dimethyl ether.

The Y zeolite useful in the production of dimethyl ether is well known and a typical synthetic zeolite usually prepared in the sodium form, that is, with a sodium cation in close proximity to each aluminum tetrahedron thereby balancing its charge. Type Y zeolite has a ratio of $Al_2O_3$ to $SiO_2$ in the range of about $Al_2O_3/3.0$–$6.0$ $SiO_2$ and an effective pore size of approximately 7.4 Angstroms.

In the integrated process for producing dimethyl ether from syngas a commercial methanol catalyst, having copper oxide, zinc oxide and aluminum oxide as components is combined with Y zeolite, a clay component, preferably Bentonite, and sufficient water to form a paste which is then extruded, dried and then calcined to provide a catalyst mixture. The copper oxide is present in a range of about 20 percent by weight to about 40 percent by weight, preferably about 25 percent by weight to about 35 percent by weight. The zinc oxide is present in a range of about 5 percent by weight to about 25 percent by weight, preferably about 10 percent by weight to about 20 percent by weight. The aluminum oxide is present in a finite range of up to about 15 percent by weight, preferably up to about 10 percent by weight. The Y zeolite is present in a range of about 1 percent by weight to about 20 percent by weight, preferably about 5 percent by weight to about 15 percent by weight. The clay is present in a range of about 30 percent by weight to about 50 percent by weight, preferably about 35 percent by weight to about 45 percent by weight.

Generally water is added in an amount sufficient to produce a paste. The paste is thoroughly mixed and extruded. The extrudate is dried at a temperature in the range of about 90° C. to about 150° C., preferably in a range of about 100° C. to about 140° C., and most preferably about 110° C. to about 130° C. for a time in the range of about 1 to about 5 hours, more preferably about 2 to about 4 hours. The dried extrudate is then calcined at a temperature in the range of about 300° to about 400° C., preferably about 325° C. to about 375° C. for a time in the range of about 1 to about 5 hours, preferably about 2 to about 4 hours.

In the reaction to convert syngas to dimethyl ether a feed gas having about 15 to about 35 volume percent CO, about 1 to about 10 volume percent $CO_2$ and about 60 to about 80 volume percent $H_2$ at a mole ratio of $H_2$:CO in a range of about 1.5 to about 4.0, preferably about 2.0 to about 3.8 is contacted in the presence of a calcined catalyst composition of an extruded mixture of copper oxide, zinc oxide, aluminum oxide, Y zeolite and clay under conversion conditions of reaction temperature in the range of about 240° C. to about 300° C., preferably about 260° C. to about 280° C. at a pressure of about 300 psig to about 1500 psig, preferably from bout 400 psig to about 1000 psig and a feed rate in a range of about 50 cc/min to about 400 cc/min.

The effluent from the reaction to convert syngas to dimethyl ether can be fed to a second reaction zone in which the catalyst is based on a silicoaluminophosphate (SAPO) material. SAPO catalysts exhibit properties of both aluminosilicate zeolites and aluminophosphates. SAPO material has a three dimensional microporous crystal framework structure of $PO_2$, $AlO_2$ and $SiO_2$ tetrahedral units. The chemical composition (anhydrous) is: $mR:(Si_xAL_yP_z)O_2$ wherein "R" represents at least one organic templating agent present in the intracrystalline pore system; "m" represents the moles of R present per mole of $(Si_xAL_yP_z)O_2$ and has a value of from zero to 0.3, the maximum value depending on the molecular dimensions of the templating agent and the available void volume of the pore system of the particular SAPO species involved, and the "x", "y" and "z" represent the mole fractions of silicon, aluminum and phosphorus, respectively. Further details of the formation of SAPO compositions can be found in U.S. Pat. No. 4,440,871, the entire disclosure of which is expressly incorporated herein by reference.

Examples of such templating agents include, but are not limited to, tetramethylammonium hydroxide, tetraethylammonium hydroxide and tetrapropylammonium hydroxide. Further details relating to the formation of SAPO compositions, including molar amounts of each oxide source, can be found in Lok et al., U.S. Pat. No. 4,440,871, the entire disclosure of which is expressly incorporated herein by reference.

Among the SAPO compositions useful in the present invention are SAPO-4, SAPO-5, SAPO-11, SAPO-16, SAPO-17, SAPO-20, SAPO-31, SAPO-34, SAPO-35, SAPO-37, SAPO-40, SAPO-41, SAPO-42 and SAPO-44. Most preferred at present is SAPO-34

The SAPO compositions can be chosen from the silicoaluminaphosphate materials per se or these materials can be modified by the inclusion of other chemical entities found effective to enhance the conversion of CO in the syngas or to affect the selectivity of the product to increase the amount of desired light olefins. Among the materials that have been determined to effect these results when combined with the SAPO compositions are lanthanum(III) nitrate hexahydrate, magnesium hydrate hexahydrate, tributyl borate and triethyl phosphate. Each of these materials can be combined with the SAPO compositions by admixing in the presence of a suitable liquid carrier which can be chosen from water and various organic liquids such as n-hexane or cyclohexane to form a paste. After thorough mixing the paste formed can be dried and later calcined into a particulate catalyst.

In general the amounts of compounds added to the SAPO compositions are in the range of about 2.0 percent by weight lanthanum to about 3.0 percent by weight lanthanum; about 1.5 percent by weight magnesium to about 2.5 percent by weight magnesium; about 3.5 percent by weight to about 4.5 percent by weight phosphorus and about 4.5 percent by weight to about 5.5 percent by weight boron. The drying is carried out at an elevated temperature of up to about 150° C., preferably up to 120° C. for a time of about 1 to about 5 hours, preferably about 2 to about 4 hours. The calcining is carried out at an elevated temperature of up to about 600° C., preferably up to about 550° C. for a time in the range of about 1 to about 5 hours, preferably about 2 to about 4 hours.

The further conversion of the effluent from contact with a first catalyst bed having as components copper oxide, zinc oxide and aluminum oxide with a combination of Y zeolite and a clay is carried out by passing the effluent from the first catalyst bed through a second catalyst bed having the above described SAPO or modified SAPO components. In general the reaction conditions for the reaction with the second catalyst composition are a flow rate in the range of about 50 cc/min to about 200 cc/min, a reaction temperature in the range of about 300° C. to about 650° C., preferably about 350° C. to about 600° C. at a pressure in the range of about atmospheric up to about 350 psig, preferably up to about 300 psig. It has been found that one of the preferred means for increasing the selectivity to light olefins is to lower the pressure on the effluent from the first reaction bed before the effluent enters the second reaction bed. Lowering this pressure to atmospheric has been found very effective to increase the selectivity to light olefins in the second reaction.

The following examples illustrate the effectiveness of the invention.

EXAMPLE I

Catalyst A: 5 g. of C79-5, a methanol synthesis catalyst commercially available from UCI characterized as containing zinc oxide, copper oxide and aluminum oxide was mixed with 3.5 g of gamma $Al_2O_3$, 1.5 g of Bentonite and 8.5 ml of water to form a paste. The paste was extruded by syringe, dried at 120° C. for 3 hours and calcined at 350° C. for 3 hours to provide an activated catalyst.

Catalyst B: 5 g. of C79-5, a methanol synthesis catalyst commercially available from UCI characterized as containing zinc oxide, copper oxide and aluminum oxide was mixed with 3.5 g of a Y zeolite embedded in clay commercially available from Grace Davison, 1.5 g of Bentonite and 8.5 ml of water to form a paste. The paste was extruded by syringe, dried at 120° C. for 3 hours and calcined at 350° C. for 3 hours to provide an activated catalyst.

A tube reactor packed with catalyst A was pretreated with a flow of about 150 cc/min of hydrogen at a temperature of 240° C. The hydrogen was replaced by a synthesis gas (syngas) having a volume composition of 20.1 percent CO, 5.1 percent $CO_2$ and 74.8 percent $H_2$ which was passed through the reactor at a rate of 190 cc/min. under reaction conditions of 270° C. and 500 psig to produce dimethyl ether (DME).

The conversion reaction was repeated duplicating the reaction conditions using a tube reactor packed with catalyst B.

The results are set out in Table I below:

TABLE I

| Run | Catalyst | CO Conv. Vol. % | Selectivity to DME, Wt. % | Selectivity to MeOH, Wt. % | Selectivity to HC, Wt. % |
|---|---|---|---|---|---|
| 1 Comp. | A | 68.5 | 55.4 | 44.0 | 0.6 |
| 2 Invention | B | 79.2 | 87.7 | 12.0 | 0.3 |

Comp. = Comparison; Conv. = Conversion

EXAMPLE II

Catalyst B was prepared as described above.

Catalyst C was C79-5, a methanol synthesis catalyst commercially available from UCI characterized as containing zinc oxide, copper oxide and alumina.

Catalyst D was prepared by mixing 10 g of SAPO-34 with 10 g Ludox AS-40 ($SiO_2$), extruding the mixture and calcining the extrudate for 6 hours at 538° C.

A tube reactor was packed with a first portion of catalyst C and a downstream portion of catalyst D. The reactor was pretreated with a flow of about 150 cc/min of hydrogen at a temperature of 240° C. The hydrogen was replaced by a synthesis gas (syngas) having a volume composition of 20.1 percent CO, 5.1 percent $CO_2$ and 74.8 percent $H_2$ which was passed through the reactor at a rate of 190 cc/min. under reaction conditions of 280° C. and 300 psig for catalyst C and 385° C. and 300 psig for catalyst C to produce light olefins.

The conversion reaction was repeated duplicating the reaction conditions for catalyst C using a tube reactor packed with catalyst B alone and then repeated again duplicating the reaction conditions for the combination of catalyst C and catalyst D using a tube packed with catalyst B substituted for Catalyst C and a downstream portion of catalyst D.

The results are set out in Table II below:

TABLE II

| Run | Catalyst in Bed I | Catalyst in Bed II | CO Conv. Vol. % | Select. Wt % $C_1$-$C_4$ | Select. Wt. % $C_2^=$-$C_4^=$ | Select. Wt. % $C_5^+$ | Select. MeOH & DME |
|---|---|---|---|---|---|---|---|
| 1 Comp. | C | D | 7.1 | 23.1 | 56.5 | 20.4 | — |
| 2 Comp. | B | None | 51.8 | 0.9 | — | 0.2 | 99.0 |
| 3 Inv. | B | D | 51.4 | 11.9 | 69.3 | 18.2 | 0.58 |

Conv. = Conversion;
Select. = Selectivity;
Comp. = Comparison:
Inv. = Invention

The inventive Catalyst B provided both an increase in conversion of CO and in the selectivity of conversion to DME as compared to Catalyst A, the catalyst commonly used in the conversion of syngas to DME.

The inventive combination of catalyst B followed by catalyst D provided a dramatic increase in both the conversion of CO and in the selectivity of conversion to $C_2^=$-$C_4^=$ hydrocarbons as compared to the combination of catalyst C followed by catalyst D or by using catalyst B alone.

EXAMPLE III

Catalyst A, Catalyst B and Catalyst D were as set out above.

For run 1 a tube reactor was packed with a first portion of catalyst B and a downstream, second portion of catalyst D. The reactor was pretreated with a flow of about 150 cc/min of hydrogen at a temperature of 240° C. The hydrogen was replaced by a synthesis gas (syngas) having a volume composition of 20.1 percent CO, 5.1 percent $CO_2$ and 74.8 percent $H_2$ which was passed through the reactor at a rate of 190 cc/min. under reaction conditions of 280° C. and 300 psig for Bed I and 385° C and 300 psig for Bed II to produce light olefins.

For run 2 a tube reactor was packed with a first portion of catalyst B and a downstream portion of catalyst D. The reactor was pretreated with a flow of about 150 cc/min of hydrogen at a temperature of 240° C. The hydrogen was replaced by a synthesis gas (syngas) having a volume composition of 20.1 percent CO, 5.1 percent $CO_2$ and 74.8 percent $H_2$ which was passed through the reactor at a rate of 190 cc/min. to produce light olefins under reaction conditions of 280° C. and 300 psig for Bed I and raising the temperature of the effluent to 385° C. and lowering the pressure of the effluent to atmospheric pressure for Bed II.

The results are set out in Table III below:

TABLE III

| Run | Catalyst | React. Temp. ° C. | React. Press. Bed I psig | React. Press. Bed II psig | CO Conv. Vol. % | Select. Wt % $C_2^-$ | Select. Wt % $C_3^-$ | Select. Wt % $C_4^-$ |
|---|---|---|---|---|---|---|---|---|
| 1 Comp | Cat B Bed I; Cat D Bed II | 280 Bed I; 385 Bed II | 300 | 300 | 51.4 | 13.1 | 31.2 | 25.0 |
| 2 Inv. | Cat B Bed I; Cat D Bed II | 280 Bed I; 385 Bed II | 300 | Atm. | 56.0 | 32.3 | 40.4 | 15.7 |

Conv. = Conversion;
Select. = Selectivity;
Comp. = Comparison;
Inv. = Invention;
Cat = Catalyst In the two bed, two temperature process to convert syngas to light olefins was predominately the $C_2$ and $C_3$ olefins produced and the CO conversion were increased by depressurizing the first bed effluent before contacting it with the second bed.

EXAMPLE IV

Catalyst B was produced mixing 15 g of C79-5, a methanol synthesis catalyst commercially available from UCI characterized as containing zinc oxide, copper oxide and alumina with 15 g of a Y zeolite embedded in clay commercially available from Grace Davison, 4.5 g of Bentonite and 25 ml of water to form a paste. The paste was extruded, dried at 120° C. for 3 hours and calcined at 350° C. for 3 hours to provide an activated catalyst.

Catalyst D was produced as set out above.

Catalyst E: 2 g of catalyst D was mixed with 2.13 g of tributyl borate and 3 g of n-hexane, dried on a hot plate, treated at 120° C. for 3 hours and calcined at 540° C. for 3 hours to produce an active catalyst.

Catalyst F: 2 g of catalyst D was mixed with 0.35 g of triethyl phosphate and 3 g of cyclohexane, dried at 120° C. for 3 hours and calcined at 540° C. for 3 hours to produce an active catalyst.

For run 1 a tube reactor was packed with a first portion of catalyst B and a downstream, second portion of catalyst D. The reactor was pretreated with a flow of about 150 cc/min. of hydrogen at a temperature of 240° C. The hydrogen was replaced by synthesis gas (syngas) having a volume composition of 20.1 percent CO, 5.1 percent $CO_2$ and 74.8 percent H2 which was passed through the reactor at a rate of 190 cc/min under reaction conditions of 280° C. and 300 psig for Bed I and 385° C. and 300 psig for Bed II to produce light olefins.

For run 2 a tube reactor was packed with a first portion of catalyst B and a downstream, second portion of catalyst E. The reactor was pretreated with a flow of about 150 cc/min. of hydrogen at a temperature of 240° C. The hydrogen was replaced by synthesis gas (syngas) having a volume composition of 20.1 percent CO, 5.1 percent $CO_2$ and 74.8 percent $H_2$ which was passed through the reactor at a rate of 190 cc/min under reaction conditions of 280° C. and 300 psig for Bed I and 385° C. and 300 psig for Bed II to produce light olefins.

For run 3 a tube reactor was packed with a first portion of catalyst B and a downstream, second portion of catalyst D. The reactor was pretreated with a flow of about 150 cc/min. of hydrogen at a temperature of 240° C. The hydrogen was replaced by synthesis gas (syngas) having a volume composition of 20.1 percent CO, 5.1 percent $CO_2$ and 74.8 percent $H_2$ which was passed through the reactor at a rate of 76 cc/min under reaction conditions of 280° C and 500 psig for Bed I and 450° C. and atmospheric pressure for Bed II to produce light olefins.

For run 4 a tube reactor was packed with a first portion of catalyst B and a downstream, second portion of catalyst F. The reactor was pretreated with a flow of about 150 cc/min. of hydrogen at a temperature of 240° C. The hydrogen was replaced by synthesis gas (syngas) having a volume composition of 20.1 percent CO, 5.1 percent $CO_2$ and 74.8 percent H2 which was passed through the reactor at a rate of 76 cc/min under reaction conditions of 280° C. and 500 psig for Bed I and 450° C. and atmospheric pressure for Bed II to produce light olefins.

The results are set out in Table IV below:

TABLE IV

| Run | Catalyst in Bed I | Catalyst in Bed II | Reaction Temp. °C | Reaction Pressure psig | CO Conv. Vol. % | $C_2^=-C_3^=$ Select. Wt % | $C_3^=/C_2^=$ |
|---|---|---|---|---|---|---|---|
| 1 Comp. | B | D | 280 Bed I, 385 Bed II | 300 Bed I, 300 Bed II | 51.4 | 69.3 | — |
| 2 Inv. | B | E | 280 Bed I, 385 Bed II | 300 Bed I, 300 Bed II | 50.4 | 76.3 | — |
| 3 Comp. | B | D | 280 Bed I, 450 Bed II | 500 Bed I, 0 Bed II | 80.6 | 77.2 | 0.60 |
| 4 Inv. | B | F | 280 Bed I, 450 Bed II | 500 Bed I, 0 Bed II | 78.4 | 79.0 | 0.67 |

Conv. = Conversion;
Select. = Selectivity;
Comp. = Comparison;
Inv. = Invention

Even though the conversion of CO was reduced using the combination of catalyst B with catalysts E and F as compared to the results using the combination of catalyst B with catalyst D, the selectivity to $C_2$ and $C_3$ olefins was increased and the ratio of $C_3/C_2$ olefins increased using catalyst F as compared to using catalyst D in the second bed.

EXAMPLE V

Catalyst B was produced mixing 10 g of C79-5, a methanol synthesis catalyst commercially available from UCI characterized as containing zinc oxide, copper oxide and alumina with 10 g of a Y zeolite embedded in clay commercially available from Grace Davison, 3.0 g of Bentonite and 15 ml of water to form a paste. The paste was extruded, dried at 120° C. for 3 hours and calcined at 350° C. for 3 hours to provide an activated catalyst.

Catalyst D was produced as set out above.

Catalyst G: 2 g of catalyst D was mixed with 0.187 g of $LaN_3O_9 6H_2O$ and 3.5 ml of $H_2O$, dried at 120° C. for 3 hours and calcined at 540° C. for 3 hours to produce an active catalyst.

Catalyst H: 2 g of catalyst D was mixed with 0.63 g of $Mg(NO_3)_2 6H_2O$ and 4 ml of $H_2O$, dried at 120° C. for 3 hours and calcined at 540° C. for 3 hours to produce an active catalyst.

For run I a tube reactor was packed with a first portion of catalyst B and a downstream, second portion of catalyst D. The reactor was pretreated with a flow of about 150 cc/min. of hydrogen at a temperature of 240° C. The hydrogen was replaced by Synthesis gas (syngas) having a volume composition of 20.1 percent CO, 5.1 percent $CO_2$ and 74.8 percent $H_2$ which was passed through the reactor at a rate of 76 cc/min under reaction conditions of 280° C. and 500 psig for Bed I and 450° C. and atmospheric pressure for Bed II to produce light olefins.

For run 2 a tube reactor was packed with a first portion of catalyst B and a downstream, second portion of catalyst G. The reactor was pretreated with a flow of about 150 cc/min. of hydrogen at a temperature of 240° C. The hydrogen was replaced by Synthesis gas (syngas) having a volume composition of 20.1 percent CO, 5.1 percent $CO_2$ and 74.8 percent $H_2$ which was passed through the reactor at a rate of 76 cc/min under reaction conditions of 280° C. and 500 psig for Bed I and 450° C. and atmospheric pressure for Bed II to produce light olefins.

For run 3 a tube reactor was packed with a first portion of catalyst B and a downstream, second portion of catalyst H. The reactor was pretreated with a flow of about 150 cc/min. of hydrogen at a temperature of 240° C. The hydrogen was replaced by Synthesis gas (syngas) having a volume composition of 20.1 percent CO, 5.1 percent $CO_2$ and 74.8 percent $H_2$ which was passed through the reactor at a rate of 76 cc/min under reaction conditions of 280° C. and 500 psig for Bed I and 450° C. and atmospheric pressure for Bed II to produce light olefins.

the results are set out in table V below:

TABLE V

| Run | Catalyst Bed I | Catalyst Bed II | Reaction Temp. °C | Reaction Pressure psig | CO Conv. Vol. % | $C_2^=-C_3^=$ Select. Wt % | $C_3^=/C_2^=$ |
|---|---|---|---|---|---|---|---|
| 1 Cont. | B | D | 280 Bed I, 450 Bed II | 500 Bed I, 0 Bed II | 80.6 | 77.2 | 0.60 |
| 2 | B | G | 280 | 500 | 82.4 | 77.7 | 0.81 |

TABLE V-continued

| Run | Catalyst Bed I | Catalyst Bed II | Reaction Temp. ° C. | Reaction Pressure psig | CO Conv. Vol. % | $C_2^=$–$C_3^=$ Select. Wt % | $C_3^=/C_2^=$ |
|---|---|---|---|---|---|---|---|
| Inv. | | | Bed I, 450 Bed II 280 | Bed I, 0 Bed II 500 | | | |
| 3 Inv. | B | H | Bed I, 450 Bed II | Bed I, 0 Bed II | 80.5 | 76.3 | 0.74 |

Conv. = Conversion;
Select. = Selectivity;
Cont. = Control;
Inv. = Invention

The results show that the ratio of $C_3/C_2$ olefins increased while the selectivity to $C_2$–$C_3$ olefins remained almost constant using catalysts G and H in the second bed in combination with catalyst B in the first bed as compared to using catalyst D in the second bed in combination with catalyst B in the first bed.

That which is claimed is:

1. A catalyst suitable for the conversion of syngas comprising zinc oxide, copper oxide, aluminum oxide, Y zeolite and clay.

2. A catalyst suitable for the conversion of syngas to light olefins comprising (A) a first catalyst bed comprising zinc oxide, copper oxide, aluminum oxide, Y zeolite and clay arranged to emit effluent into (B) a second catalyst bed comprising a SAPO.

3. A catalyst system according to claim 2 wherein (B) the second catalyst bed is chosen from the group consisting of SAPO-34 and modified SAPO-34.

4. A catalyst system according to claim 3 wherein the second catalyst bed is a modified SAPO-34 chosen from the group consisting of SAPO-34 modified with lanthanum(III) nitrate hexahydrate; SAPO-34 modified with magnesium nitrate hexahydrate; SAPO-34 modified with tributyl borate and SAPO-34 modified with triethyl phosphate.

5. A catalyst system according to claim 4 wherein the second catalyst bed is SAPO-34 modified with lanthanum (III) nitrate hexahydrate.

6. A catalyst system according to claim 4 wherein the second catalyst bed is SAPO-34 modified with magnesium nitrate hexahydrate.

7. A catalyst system according to claim 4 wherein the second catalyst bed is SAPO-34 modified with tributyl borate.

8. A catalyst system according to claim 4 wherein the second catalyst bed is SAPO-34 modified with triethyl phosphate.

* * * * *